United States Patent [19]

Lutz

[11] Patent Number: 5,832,051
[45] Date of Patent: Nov. 3, 1998

[54] METHOD AND APPARATUS FOR RADIOLOGICAL EXAMINATION OF CARDIAC PHASES OF A PATIENT

[75] Inventor: Andreas Lutz, Poxdorf, Germany

[73] Assignee: Siemens Aktiengesellschaft, Munich, Germany

[21] Appl. No.: 848,872

[22] Filed: May 1, 1997

[30] Foreign Application Priority Data

May 31, 1996 [DE] Germany .................. 196 22 075.0

[51] Int. Cl.$^6$ ................................................ G01N 23/00
[52] U.S. Cl. ............................................ 378/8; 378/95
[58] Field of Search ............................................ 378/8, 95

[56] References Cited

U.S. PATENT DOCUMENTS 3,952,201  4/1976  Hounsfield .................................. 378/8
4,547,892  10/1985  Richey et al. .

FOREIGN PATENT DOCUMENTS

OS 44 42 287  5/1996  Germany .

Primary Examiner—Craig E. Church
Attorney, Agent, or Firm—Hill & Simpson

[57] ABSTRACT

In a method and an apparatus for the radiological examination of individual cardiac phases of a patient, an X-ray beam is rotated around and penetrates the heart of a patient from various angular positions and the attenuated X-ray beam strikes a radiation detector. The cardiac rhythm of the patient is determined in order to set the rotation time of the X-ray beam around the patient and to produce various control signals synchronized to the cardiac rhythm of the patient, so that radiological exposures of various cardiac phases are possible for the duration of a measurement interval. The setting of the rotation time of the X-ray beam so that the rotation time is larger or smaller, by the measurement interval, than the cycle time of the cardiac rhythm of the patient, so that after a few rotations there is a phase displacement of 360° between the rotating X-ray beam and the cardiac rhythm of the patient. Projection groups of a partial or complete rotation of the respective cardiac phases are subsequently formed from the measurement data of projections of various cardiac phases for the duration of the measurement interval from which images of the respective cardiac phase are reconstructed.

8 Claims, 3 Drawing Sheets

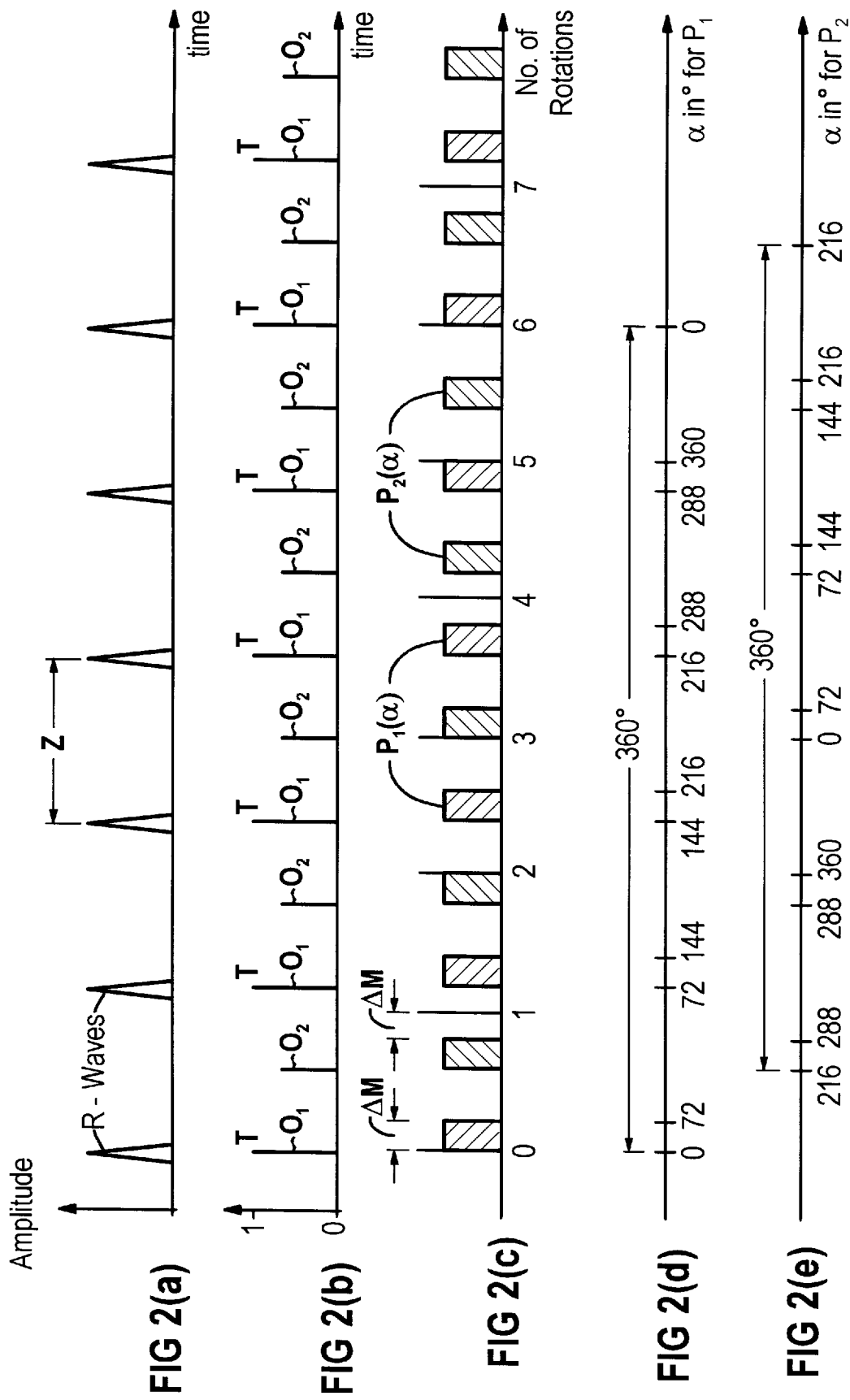

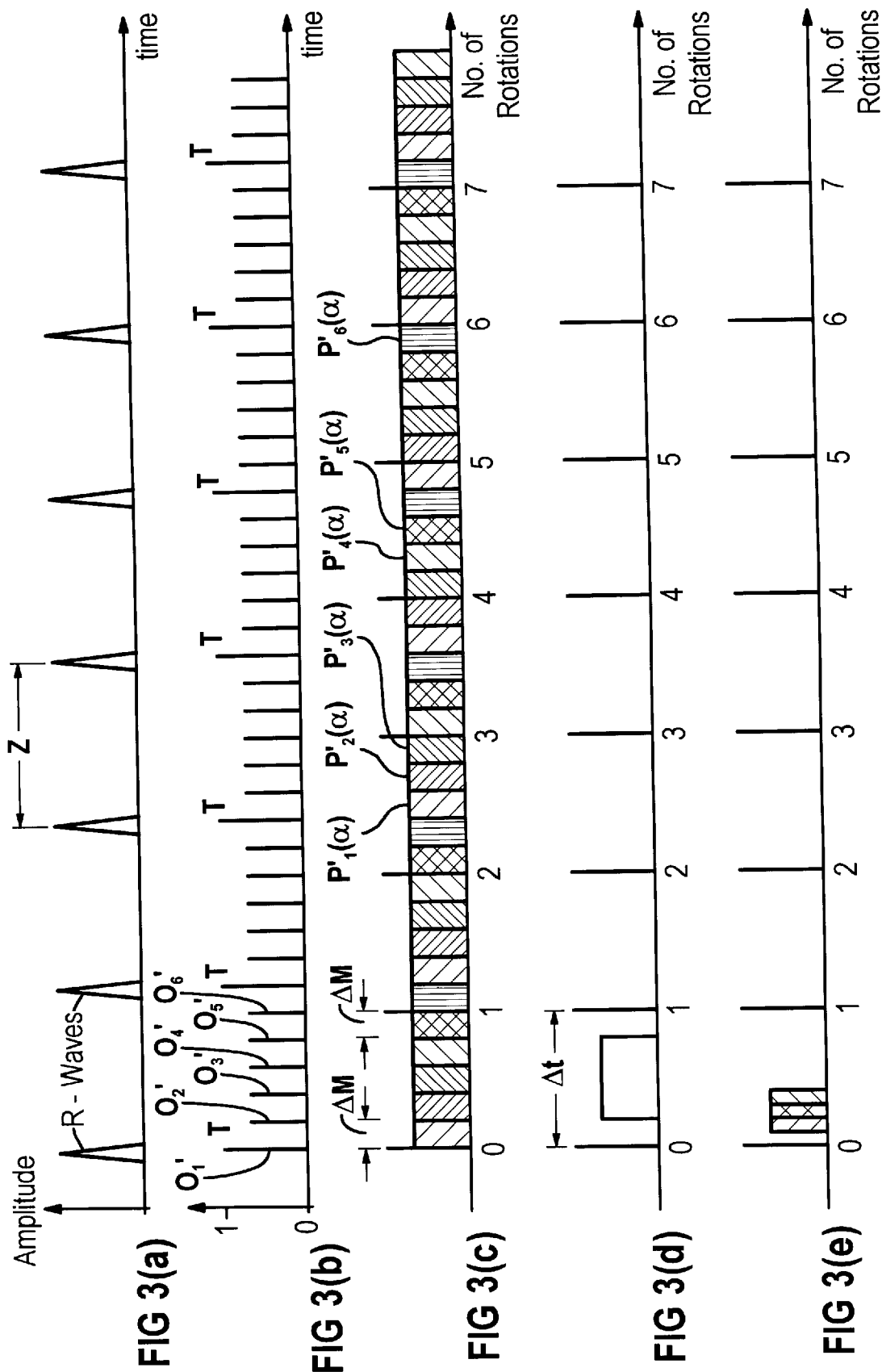

METHOD AND APPARATUS FOR RADIOLOGICAL EXAMINATION OF CARDIAC PHASES OF A PATIENT

BACKGROUND OF THE INVENTION

1. Field of the Invention

The present invention is directed to a method and apparatus for the radiological examination of individual cardiac phases of a patient of the type wherein an X-ray beam is rotated around the patient so as to penetrate the heart of the patient from different angular positions within a half rotation to several rotations of the X-ray beam around the patient, the attenuated X-ray beam then strikes a radiation detector.

2. Description of the Prior Art

In known methods and systems of the above type, the cardiac rhythm of the patient is determined for use in setting the rotation time of the X-ray beam about the patient and in order to produce various control signals synchronized with the patient's cardiac rhythm, so that radiological exposures of projections of different cardiac phases are possible. Images of the individual cardiac phases are subsequently reconstructed from the projections of the various cardiac phases exposed at the various angle positions.

Methods for imaging cardiac phases are also known from nuclear medicine. German OS 44 42 287 for example, discloses a method of this sort for cardiac imaging with a gamma camera having a rotating collimator that has collimator channels positioned obliquely in relation to the axis of rotation.

A method and apparatus of the above type are known for example from German OS 24 34 639, in which, for the radiological examination of a patient's heart, a rectangular signal is derived from the electrocardiogram (ECG) thereof, this signal reflecting the duration of the heartbeat and a period following the heartbeat with a relatively smaller heart motion. This rectangular signal is supplied to a radiological measurement system that rotates around the patient, and radiological exposures of the heart always take place only when the heart is in the period of relatively smaller motion, in order to avoid exposures with local blurring in the imaging due to excessively rapid heart motion. The rotational speed of the measurement system rotating around the patient is controlled such that, as far as possible, the patient's heart is transilluminated at least once from all angular positions in several rotations of the measurement system around the patient.

In addition, from German OS 28 13 830 an arrangement is known for producing cardiac exposures of a patient with X-rays or gamma rays, in which the scanning data are produced continuously during the rotation of the source of radiation and of the detectors about the patient. An EKG signal from the patient is thereby used as a time basis by an image processing unit for controlling the data storage during a suitable phase in a cardiac cycle of the patient.

These known methods and devices employ an expensive control arrangement for influencing the rotation time, or for adapting the rotation time of the X-ray source or of the X-ray beam to the cycle time of the patient's cardiac rhythm and due to the inertia of the measurement system, it is not possible to examine arbitrary cardiac phases of a patient. Moreover, during measurement with large numbers of rotations of the X-ray source or of the X-ray beam around the patient, large amounts of redundant data are obtained. The exposure times of all projections of the individual cardiac phases required for the reconstruction of an image thereby become very long. A large computing expense for the reconstruction of an image of a cardiac phase also results.

SUMMARY OF THE INVENTION

An object of the present invention is to provide a method and apparatus of the above general type with which arbitrary cardiac phases of a patient can be examined radiologically with shortened exposure times and faster image reconstruction.

According to the invention, this object is achieved in a method for the radiological examination of individual cardiac phases of a patient, in which an X-ray beam, which penetrates the patient's heart from various angular positions within a half rotation to several rotations of the X-ray beam about the patient, then strikes a radiation detector, the method including the following steps.

The cycle time of the cardiac rhythm of the patient is determined and setting of the rotation time of the X-ray beam rotating about the patient so that the rotation time is made larger or smaller, by a predeterminable measurement interval, than the cycle time of the cardiac rhythm of the patient, so that, dependent on the rotation time, after a few rotations there is a phase difference of 360° between the rotating X-ray beam and the patient's cardiac rhythm. A trigger signal containing trigger impulses is generated, which is synchronized with the cardiac rhythm of the patient. Predetermined control signals for the examination of various cardiac phases are generated chronologically displaced in relation to the trigger pulses of the trigger signal. Exposure and storage of measurement data of projections of various cardiac phases take place for the duration of the measurement interval within each rotation of the X-ray beam around the patient. The measurement data of the projections of the respective cardiac phases, exposed and stored at various angular positions during several rotations of the X-ray beam, are combined to form projection groups of a partial or complete rotation. Images of a respective cardiac phase are reconstructed from the measurement data of the projection groups of a partial or complete rotation of the respective cardiac phase, on the basis of the cycle time of the trigger signal, the cycle time of the control signal relative to the trigger signal, and the measurement interval.

By selection of the duration of a measurement interval that indicates the time resolution of a cardiac phase to be examined, cardiac phases can be radiologically examined with a high (short measurement interval) dynamic (motion activity) or with a comparatively low (long measurement interval) dynamic. The larger the measurement interval is, the fewer rotations of the X-ray beam around the patient are required for the radiological examination of a cardiac phase. By the predetermined emission of several control signals for one a trigger pulse of the trigger signal, which pulse is synchronized to the cardiac rhythm of the patient, projections of various cardiac phases can be exposed in one rotation of the X-ray beam about the patient, with the duration of the measurement interval being substantially the same for all cardiac phases. In a short time and with only a few rotations, complete images of various cardiac phases thus can be reconstructed from the recorded measurement data of the projections. Because generally the angle intervals in which projections are exposed in several rotations of the X-ray beam around the patient do not overlap, or do so only insignificantly, the radiation dose to which the patient is exposed during the examination is reduced, and the quantity of redundant measurement data of various exposed cardiac phases is also reduced. The combination of projections of various cardiac phases to form projection groups of a partial or complete rotation is thus simplified, and the reconstruction of images of the respective cardiac phases is accelerated. If an examination of all phases of the cardiac rhythm of a patient is desired, the exposure and storage of the measurement data of the projections during a rotation of the X-ray beam about the patient takes place continuously. The control signals, the measurement interval and the cycle time of the trigger signal are then used for the reconstruction of the images of the various cardiac phases from the sequence of the exposed projections, so that a sequence of images of all cardiac phases is obtained.

An inventive computer tomography apparatus for implementing the inventive method has a radiological measurement system that rotates around an axis of rotation, with measurement means for determining the cycle time of the cardiac rhythm of the patient, setting means for setting the rotation time of the measurement system around the axis of rotation, and means for setting a measurement interval and emitting control signals in a predetermined chronological relation to a trigger signal synchronized to the patient's cardiac rhythm for the examination of various cardiac phases. The apparatus has control means for exposing and storing measurement data, produced at different projection angles for various cardiac phases for the duration of the measurement interval within each rotation of the measurement system around the axis of rotation. The apparatus further has means for reconstructing images of a respective cardiac phase from the various stored measurement data of the projections for a half rotation to several rotations of the measurement system around the axis of rotation during the respective cardiac phase to be imaged.

In an embodiment of the invention, the measurement system rotating about the axis of rotation contains a source of X-ray radiation and a radiation detector, the X-ray source emits a fan-shaped beam of X-rays that penetrates the patient's body and strikes the radiation detector.

In a preferred embodiment of the invention, an electrocardiograph and electrodes connected therewith are used to determine the cycle time of the cardiac rhythm of the patient, and to use two computers that exchange data with one another are used to form the setting means for setting the rotation time, the means for setting a measurement interval and emitting control signals, the control means for recording and storing measurement data from projections of various cardiac phases, and the means for the reconstruction of images of a respective cardiac phase.

DESCRIPTION OF THE DRAWINGS

FIGS. 2(a)–2(e) respectively show diagrams for the chronological sequence of the inventive method and for explanation of the manner of operation of the apparatus shown in FIG. 1.

FIGS. 3(a)–3(e) respectively show diagrams for the chronological sequence of the inventive method and for the explanation of the manner of operation of the apparatus shown in FIG. 1, with graphing of all phases of the cardiac rhythm of a patient.

DESCRIPTION OF THE PREFERRED EMBODIMENTS

Figure 1:
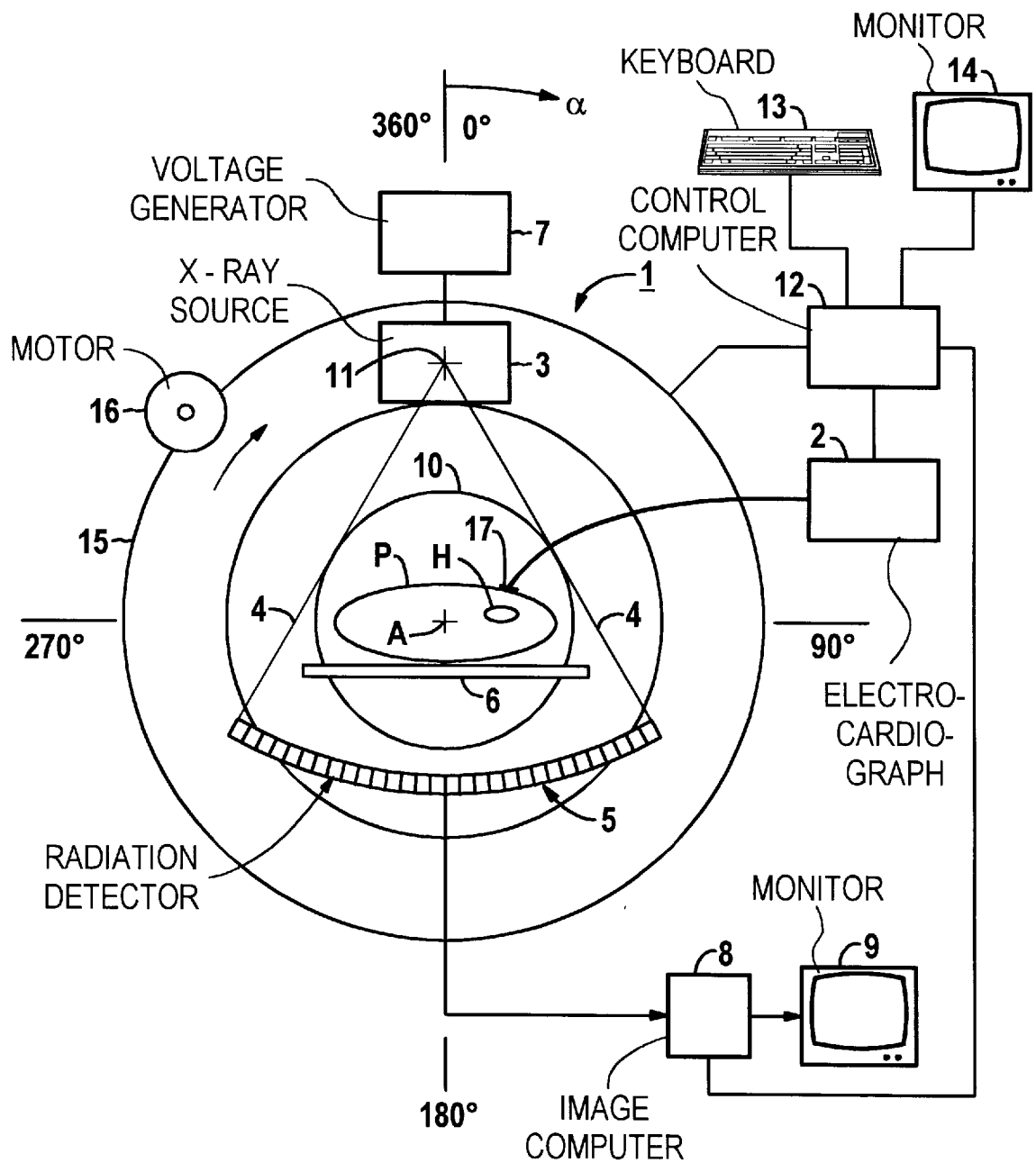
FIG. 1 is a schematic block diagram of an inventive apparatus for conducting the inventive method for the radiological examination of individual cardiac phases of a patient.

FIG. 1 shows an inventive apparatus for conducting the inventive method for the radiological examination of individual cardiac phases of a patient P, in the form of a computed tomography apparatus 1 and an electrocardiograph 2. The computed tomography apparatus 1 has a measurement system consisting of an X-ray source 3 that emits a fan-shaped beam of X-rays 4 and of a radiation detector 5 formed by a series of individual detectors, e.g. 1024 individual detectors. Controlling of the computed tomography apparatus 1 ensues by means of a control computer 12. The control computer 12 is connected to an input unit, such as a keyboard 13, and to a monitor 14. The focus of the X-ray source 3, from which the X-ray beam 4 emanates, is designated 11. The patient P to be examined lies on a patient bed 6.

In order to conduct, in general, a radiological examination of a patient P, the measurement system is rotated 360° around a measurement field 10 in which the patient P lies. For this purpose, a motor 16 drives the rotating gantry 15. The axis of rotation, which is at a right angle to the fan-shaped X-ray beam 4, is designated A. The X-ray source 3, which is fed by a voltage generator 7, is operated in pulsed fashion or with continuous radiation. At predetermined angle positions α of the measurement system projections of slices of the patient P are exposed, and the associated data sets of measurement data from the radiation detector 5 are supplied to an image computer 8 that calculates the coefficients of attenuation of predetermined image points from the data sets produced, and reproduces them graphically on a monitor 9. An image of the transilluminated slice of the patient P accordingly appears on the monitor 9.

In order to conduct a radiological examination of various cardiac phases of a patient P, electrodes 17 are connected to the patient P in the region of the heart H. The electrodes 17 are connected to the electrocardiograph 2 for the acquisition and graphing of the cycle time Z of the cardiac rhythm of the patient P. The graphing of the cardiac rhythm of the patient P ensues parallel to the radiological examination of the patient and therefore, if possible, the electrodes 17 are attached to the body of the patient P in such a way that they do not disturb the radiological examination, such as by arranging them outside the beam path of the X-ray beam 4 of the X-ray source 3.

FIGS. 2(a) and 3(a) show a measurement curve for the cardiac cycle Z of the patient P in a highly simplified form, in which, disregarding all other characteristic features of an ECG waveform of the patient P, only the R-wave is shown, which as a rule exhibits the highest amplitude in the overall ECG. By definition, the heart cycle of a patient generally begins with the R-wave and continues until the next R-wave occurs. Due to the high amplitude of the R-wave in the ECG of the patient P, which is easily acquired from the point of view of measurement technology, a trigger pulse T is produced for each R-wave of the ECG of the patient P, so that a trigger signal is obtained that is synchronized to the cardiac rhythm of the patient P (cf. FIG. 2(b) and FIG. 3(b)). The trigger signal, formed by a sequence of trigger pulses T, is supplied to the control computer 12 of the computed tomography apparatus 1 and the electrocardiograph 2, already in digital form.

During preparation for the examination of one or several different cardiac phases of the patient P, the physician uses the keyboard 13 connected with the control computer 12 to enter a measurement interval ΔM that indicates the duration of the exposure of projections of each cardiac phase to be examined per rotation of the measurement system around the axis of rotation A. The rotation time of the measurement system around the patient P, i.e., around the axis of rotation A, thus is calculated by the software of the control computer 12, this rotation time corresponds approximately to the cycle time Z of the cardiac rhythm of the patient P, shortened or lengthened by the duration of the measurement interval ΔM. In this way, in each rotation of the measurement system around the axis of rotation A, the measurement system is located, during a particular cardiac phase of a patient P, in a different angular position a in relation to the angular count, shown in FIG. 1, of the measurement field 10 of the computed tomography apparatus 1. Dependent on the duration of the measurement interval ΔM or the rotation time of the measurement system around the axis of rotation A, after some rotations of the measurement system a phase displacement of 360° is achieved between the rotating measurement system and the cardiac rhythm of the patient P. The number of rotations at which a phase displacement of 360° is achieved between the rotating measurement system and the cardiac rhythm of the patient P corresponds at least to the number of groups of projections that are exposed one after the other from various angular positions α of the measurement system and which are combined for the reconstruction of a complete image of a cardiac phase from the various rotations of the measurement system.

In the case of the exemplary embodiment of the invention, the rotation time of the measurement system, which typically lies between 0.75 seconds and 1 second, substantially corresponds to the cycle time Z of the cardiac rhythm of the patient P, shortened by the measurement interval ΔM (ΔM≈⅙ Z), and the duration of the measurement interval ΔM corresponds approximately to a fifth of the rotation time of the measurement system, so that after approximately six rotations of the measurement system around the axis of rotation A, a phase displacement of 360° is achieved between the rotating measurement system and the cardiac rhythm of the patient P. This means that about six rotations of the measurement system around the patient P suffice to create a complete image of this cardiac phase from the data sets of measurement data of projections of a cardiac phase, recorded at five different angular positions α.

After the determination of the measurement interval ΔM of each cardiac phase per rotation, and thereby the determination of the rotation time of the measurement system around the patient P, in the case of pulsed operation of the X-ray source 3 (cf. FIGS. 2(a)–2(e)) the physician determines the cardiac phases of the patient P that must be radiologically examined, for this purpose the physician orients himself or herself so as to be able to see the display of the trigger signal synchronized to the cardiac rhythm of the patient, which is shown on the monitor of the control computer 12. By selecting (setting) an appropriate one of a number of predetermined control signals, i.e. offset signals relative to a trigger pulse T, the physician determines the times at which projections of particular cardiac phases of the heart H of the patient P are exposed per rotation of the measurement system around the axis of rotation A. As can be seen from FIG. 2(c), in the present case projections $P_1(\alpha)$ and $P_2(\alpha)$ of two different cardiac phases of the patient P are exposed, whereby the value of the control signal $O_1$ for the exposure of the projections $P_1(\alpha)$ of one cardiac phase relative to a trigger pulse T of the trigger signal corresponds to zero, and the value of the control signal $O_2$ for the exposure of the projections $P_2(\alpha)$ of the other cardiac phase relative to a trigger pulse T of the trigger signal in about half the duration of the cycle time Z of the cardiac rhythm of the patient P. Also, the control signals $O_1$ and $O_2$ are periodic signals that are synchronized with the cardiac rhythm of the patient P via the trigger pulses T.

The physician begins the measurement by entering a start signal via the control computer 12, causing the measurement system to move around the patient P with the predetermined rotational speed, with projections $P_1(\alpha)$ and $P_2(\alpha)$ of the two cardiac phases to be examined being exposed per rotation of the measurement system at the selected times at various angular positions α, each exposure lasting for the duration of the measurement interval ΔM. During the rotations of the measurement system around the axis of rotation A, advancing of the patient bed 6 does not take place. FIGS. 2(d) and 2(e) respectively show, in relation to the angle count a shown in FIG. 1, the angular positions α or angular intervals Δα at which projections $P_1(\alpha)$ and $P_2(\alpha)$ of the two cardiac phases are graphed.

The data sets of the measurement data of each projection $P_1(\alpha)$ and $P_2(\alpha)$ of the sequence of projections $P_1(\alpha)$ and $P_2(\alpha)$ in an angular interval Δα of the two cardiac phases per rotation of the measurement system are read out at fixed times from the radiation detector 5, and are supplied to the computer 8, which intermediately stores the data sets. The measurement point in time of the projections $P_1(\alpha)$ and $P_2(\alpha)$ relative to the start of the measurement is also recorded and stored. The data sets of the projections $P_1(\alpha)$ and $P_2(\alpha)$ of the two cardiac phases, stored during the approximately six rotations of the measurement system are subsequently combined in the computer 8 to form projection groups of a partial or complete rotation of the respective cardiac phase, from which a partial or complete image of the cardiac phase is reconstructed in a known way. Not all the data sets of the six rotations of the measurement system are required for the reconstruction of a partial image. A half rotation of the measurement system around the patient P can already suffice for the reconstruction of a partial image.

For the reconstruction of images from the projections $P_1(\alpha)$ and $P_2(\alpha)$ of the two cardiac phases, the offset relative to the trigger impulse T ($O_1$, $O_2$), the duration of the measurement interval ΔM, and the cycle time of the trigger impulse are required, which are provided to the computer 8 via a data line from the control computer 12.

The stored projections $P_1(\alpha)$ and $P_2(\alpha)$ at an angular interval Δα thus no longer need to be subjected to angle interpolation at equidistant angle increments, since before the back-projection they were subjected to a weighting with respect to their angular difference. Thus slight overlaps or gaps of angle intervals Δα, caused e.g. by slight fluctuations of the speed of rotation of the measurement system around the axis of rotation A, can be compensated.

If it is desired, as shown in FIG. 3(c), to examine all the phases of the cardiac rhythm of a patient P, the exposure and storing of projections $P_1'(\alpha)$ to $P_6'(\alpha)$ ensues continuously during the rotation of the X-ray beam 4 about the patient P. The control signals $O_1'$ to $O_6'$, the measurement interval ΔM and the cycle time of the trigger signal are then used in order to make use of only those projections from the sequence of the projections $P_1'(\alpha)$ to $P_6'(\alpha)$, exposed during a half rotation to several rotations of the X-ray beam 4 about the patient P, that are relevant for the reconstruction of a particular image of a cardiac phase. The control signals $O_1'$ to $O_6'$ can thereby be dispensed with before the measurement, and do not need to be determined until the time of the reconstruction of images.

In addition, in this case, as shown in FIGS. 3(d) and 3(e), there is also the possibility of using all projections exposed in a time interval Δt within a rotation of the X-ray beam 4 around the patient P for the reconstruction of a desired image of a cardiac phase, or using projections repeatedly for the reconstruction of quasi-overlapping images of cardiac phases.

As already mentioned, for the exposure of projections the X-ray source 3 can be operated in pulsed fashion or with continuous radiation. In the case of pulsed operation, the X-ray source 3 is always activated by the control signals when for example, as shown in FIG. 2(c), exposures of projection $P_1(\alpha)$ or $P_2(\alpha)$ are to ensue in one of the two cardiac phases. In the case of continuous operation of the X-ray source 3, the control signals, as mentioned, are used in order to make use of only the projections of a cardiac phase, from the sequence of the projections exposed during a half rotation to several rotations about the patient of the measurement system around the patient P that are relevant for the reconstruction of a particular image. On the basis of the control signals, however, it is also possible to mechanically block or influence the X-ray beam 4, e.g. using a screen. Using the control signals it is also possible to electrically block or influence the electron beam of the X-ray source 3 that strikes a target in order to produce the X-ray beam 4. This can be accomplished, e.g., using an electron beam deflection. Such modification of the X-ray beam 4 or the electron beam used to produce ensues in a manner so that the patient P can be transilluminated, or projections can be graphed, only during the cardiac phases that are to be examined.

The measurement system does not necessarily have to be formed by an X-ray source 3, which rotates around the patient P, and a radiation detector 5, but alternatively can also be formed by a circle of stationary detectors with a rotating X-ray source, or by one or several stationary X-ray sources and rotating detectors.

If more than two cardiac phases are examined using the inventive method for radiological examination of various cardiac phases of the patient P, the following applies. The shorter the measurement interval $\Delta M$ is chosen for the examination of a cardiac phase, the more cardiac phases can be examined, or the more dynamic the examined cardiac phases can be; however, the number of rotations required for the reconstruction of a complete image of each cardiac phase is also higher. Various cardiac phases can be represented with various offset signals to a trigger pulse T of the trigger signal. Given a corresponding selection of the measurement interval $\Delta M$ and different offset signals to the trigger pulse T of the trigger signal, a sequence of images of all cardiac phases is obtained in multiple image reconstruction with the various offsets to the trigger pulse T.

Given sufficient computing power of either of the two computers 8 and 12, the other of the two computers can be dispensed with, so that only one computer controls the computed tomography apparatus 1, for the measurement of individual cardiac phases and the reconstruction of images of individual cardiac phases.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for radiologically examining individual cardiac phases of a patient, comprising the steps of:

rotating an X-ray beam around a patient and penetrating a heart of said patient from a plurality of angular positions within at least a half rotation of said X-ray beam, thereby obtaining attenuated radiation;

detecting said attenuated radiation;

determining a cycle time of cardiac rhythm of said patient;

setting a rotation time for said X-ray beam to complete a rotation around said patient so as to differ from said cycle time by a predetermined measurement interval defining the duration of said X-ray beam penetrating the patient per rotation of said X-ray beam for examining a cardiac phase for producing, after a plurality of rotations of said X-ray beam, a phase displacement of 360° between the X-ray beam and said cardiac rhythm;

generating a trigger signal synchronized with said cardiac rhythm comprising a plurality of trigger pulses;

generating at least one control signal chronologically displaced by a predetermined amount relative to each trigger pulse of said trigger signal, said control signal identifying a cardiac phase to be examined within said rhythm;

exposing said patient to said X-ray beam starting at the time of said control signal and lasting for the duration of said measurement interval within each rotation of said X-ray beam around said patient to obtain measurement data for a plurality of projections of said X-ray beam within said measurement interval, and storing said measurement data;

combining said measurement data for said projections for each rotation of said X-ray beam to form projection groups for at least a partial rotation of said X-ray beam; and reconstructing an image of the cardiac phase corresponding to said control signal from said measurement data in said projection groups dependent on a cycle time of said trigger signal, the chronological displacement of said control signal relative to said trigger pulses, and said measurement interval.

2. A method as claimed in claim 1 wherein the step of setting the rotation time of said X-ray beam around said patient comprises setting said rotation time of said X-ray beam around said patient so as to be larger than said cycle time of said cardiac rhythm by said measurement interval.

3. A method as claimed in claim 1 wherein the step of setting the rotation time of said X-ray beam around said patient comprises setting said rotation time of said X-ray beam around said patient so as to be smaller than said cycle time of said cardiac rhythm by said measurement interval.

4. A method as claimed in claim 1 wherein the step of generating at least one control signal comprises:

making available a plurality of different control signals, each control signal having a different chronological displacement relative to said trigger pulses, and each control signal causing examination of a respective cardiac phase dependent on the chronological displacement of that control signal relative to said trigger pulses; and identifying a cardiac phase to be examined, and selecting the control signal, among said plurality of control signals, having a cardiac phase associated therewith corresponding to the cardiac phase identified for examination.

5. An apparatus for radiologically examining individual cardiac phases of a patient, comprising:

means for rotating an X-ray beam around a patient for penetrating a heart of said patient from a plurality of angular positions within at least a half rotation of said X-ray beam, thereby obtaining attenuated radiation;

means for detecting said attenuated radiation;

means for determining a cycle time of cardiac rhythm of said patient;

means for setting a rotation time for said X-ray beam to complete a rotation around said patient so as to differ from said cycle time by a predetermined measurement interval defining the duration of said X-ray beam penetrating the patient per rotation of said X-ray beam for examining a cardiac phase for producing, after a plurality of rotations of said X-ray beam, a phase displacement of 360° between the X-ray beam and said cardiac rhythm;

means for generating a trigger signal synchronized with said cardiac rhythm comprising a plurality of trigger pulses;

means for generating at least one control signal chronologically displaced by a predetermined amount relative to each trigger pulse of said trigger signal, said control signal identifying a cardiac phase to be examined within said rhythm;

means for obtaining measurement data, by exposing said patient to said X-ray beam starting at the time of said control signal and lasting for the duration of said measurement interval within each rotation of said X-ray beam around said patient, for a plurality of projections of said X-ray beam within said measurement interval, and for storing said measurement data;

means for combining said measurement data for said projections for each rotation of said X-ray beam to form projection groups for at least a partial rotation of said X-ray beam; and means for reconstructing an image of the cardiac phase corresponding to said control signal from said measurement data in said projection groups dependent on a cycle time of said trigger signal, the chronological displacement of said control signal relative to said trigger pulses, and said measurement interval.

6. An apparatus as claimed in claim 5 comprising an X-ray source which emits said X-ray beam, and wherein said means for rotating said X-ray beam comprises means for rotating said X-ray source and said radiation detector around said patient.

7. An apparatus as claimed in claim 5 wherein said means for determining the cycle time of the cardiac rhythm of said patient comprises an electrocardiograph having a plurality of electrodes attachable to said patient.

8. An apparatus as claimed in claim 5 wherein said means for setting said rotation time of said X-ray beam, said means for selecting a measurement interval, said means for generating said control signals, said means for obtaining measurement data, said means for storing said measurement data, and said means for reconstructing an image are formed by two computers with means for exchanging data between said two computers.

* * * * *